United States Patent [19]

Wake et al.

[11] 4,252,717

[45] Feb. 24, 1981

[54] PREPARATION OF 2,2′-AZOBIS(2-METHYLPROPIONITRILE)

[75] Inventors: Shigeo Wake, Saijo; Shigeru Honmaru, Ooita; Hidenori Danda, Niihama, all of Japan

[73] Assignee: Sumitomo Chemical Company, Limited, Osaka, Japan

[21] Appl. No.: 34,988

[22] Filed: May 1, 1979

[30] Foreign Application Priority Data

Feb. 6, 1979 [JP] Japan .................................. 54-13035

[51] Int. Cl.³ ............................................ C07C 107/00
[52] U.S. Cl. ...................................................... 260/192
[58] Field of Search ........................................... 260/192

[56] References Cited

U.S. PATENT DOCUMENTS

| | | | |
|---|---|---|---|
| 2,711,405 | 6/1955 | Anderson | 260/192 |
| 2,713,576 | 7/1955 | DeBenneville | 260/192 |
| 3,390,146 | 6/1968 | Nield et al. | 260/192 |
| 3,937,696 | 2/1976 | Knowles et al. | 260/192 |
| 3,987,025 | 10/1976 | Moore | 260/192 |
| 4,051,124 | 9/1977 | Moore | 260/192 |
| 4,061,590 | 12/1977 | Moore | 260/192 X |

FOREIGN PATENT DOCUMENTS

| | | | |
|---|---|---|---|
| 49-20297 | 5/1974 | Japan | 260/192 |
| 672106 | 5/1952 | United Kingdom | 260/192 |

*Primary Examiner*—Paul F. Shaver
*Attorney, Agent, or Firm*—Stevens, Davis, Miller & Mosher

[57] ABSTRACT

2,2′-Azobis(2-methylpropionitrile), which is used as a foaming agent and a radical polymerization initiator, is produced in a high yield and a high purity, by (1) subjecting a crude 2-amino-2-methylpropionitrile product obtained by the reaction between acetone cyanohydrin and ammonia, to reduced pressure distillation, (2) contacting the resulting purified 2-amino-2-methylpropionitrile product having an ammonia content of 1.5% by weight or less with an aqueous metal hypochlorite solution, and then (3) treating the resulting aqueous suspension of 2,2′-azobis(2-methylpropionitrile) with a reducing agent.

4 Claims, No Drawings

PREPARATION OF 2,2'-AZOBIS(2-METHYLPROPIONITRILE)

The present invention relates to improvements in the production of 2,2'-azobis(2-methylpropionitrile). More particularly, it relates to a process for producing high-purity 2,2'-azobis(2-methylpropionitrile) in a high yield, which comprises contacting 2-amino-2-methylpropionitrile purified by distillation under reduced pressure with an aqueous solution containing a metal hypochlorite, and then treating the resulting aqueous slurry of the product with a reducing agent.

2,2'-Azobis(2-methylpropionitrile) is a useful compound which has been widely used as a foaming agent or radical polymerization initiator. Generally, azodinitrile compounds are produced in industry by oxidizing hydrazo compounds, which are produced using a hydrazine, a ketone and hydrogen cyanide as main materials, with a halogen, a hypohalite, hydrogen peroxide or the like. These methods, however, have various drawbacks. For example, expensive hydrazines are required as a starting material, and purification such as recrystallization is required to obtain pure azodinitrile compounds because unreacted hydrazo compounds are contained as impurities in the product.

Another method for producing azodinitrile compounds is disclosed in U.S. Pat. No. 2,711,405 wherein the compounds are produced by reacting a cyanohydrin of an aliphatic ketone with ammonia to form α-aminonitrile, and then reacting the α-aminonitrile with a metal hypochlorite in an aqueous medium to carry out the oxidative coupling of the nitrile compound. Similar methods are also disclosed in British Pat. No. 672,106 and Japanese Pat. Publication No. 20,297/1974.

In U.S. Pat. No. 2,711,405, the objective compound, 2,2'-azobis(2-methylpropionitrile), is obtained by (1) reacting acetone cyanohydrin with ammonia to produce 2-amino-2-methylpropionitrile, (2) distilling the resulting crude product under reduced pressure to obtain pure 2-amino-2-methylpropionitrile in a yield of 70%, and then (3) oxidizing the purified product with sodium hypochlorite to obtain te objective compound in a yeild of 85%. According to the experimental example of this patent, the yield of 2,2'-azobis(2-methylpropionitrile) is only 59.5% based on acetone cyanohydrin. This patent says that a higher concentration of the aqueous hypochlorite solution is favourable for the oxidative coupling. As shown hereinafter, however, when the concentration is high, oily substances considered as an intermediate separate out during the reaction, so that stirring the reaction system at a very high speed or lowering the reaction temperature to less the 0° C. is necessary to advance the reaction. That is, the reaction does not proceed well under mild conditions which are industrially favourable.

In British Pat. No. 672,106, the concentration of a metal hypochlorite in the oxidative coupling of α-aminonitrile is limited to less than 7%, so that the oxidative coupling proceeds under mild conditions, but the yield is low, because the α-aminonitrile is synthesized by the Jacobson method [J. Am. Chem. Soc. 68, 2628 (1946)] which is disadvantageous, as shown hereinafter, in that a large quantity of potassium hydroxide is required for the purification of 2-amino-2-methylpropionitrile and yet the yield thereof is only 77%.

In Japanese Pat. Publication No. 20,297/1974, azodinitrile compounds are produced by reacting a ketone with ammonium cyanide to obtain α-aminonitrile, and then contacting the resulting crude aqueous α-aminonitrile solution, without purification, with a metal hypochlorite. The yield of oxidative coupling is as low as 59.4% to 77.2% based on the α-aminonitrile.

As described above, these methods using α-aminonitrile are promising in that they can overcome the drawbacks peculiar to the foregoing methods using an expensive hydrazine. But they have not yet been established as a commercial process on account of the following various drawbacks: α-Aminonitrile is unstable and difficult to purify; the yield of oxidative coupling is low; and the final azodinitrile compounds have not high purity enough to be usable as initiators for the polymerization of a methacrylate or the like, and therefore purification such as recrystallization is required for such a purpose.

The inventors extensively studied to establish a commercial process for producing 2,2'-azobis(2-methylpropionitrile) which is free from the foregoing drawbacks.

As a result of detailed investigation on the effect of impurities on the oxidative coupling of 2-amino-2-methylpropionitrile, the inventors found that hydrogen cyanide or acetone contained in 2-amino-2-methylpropionitrile exerts some adverse effects on the oxidative coupling, and that ammonia markedly lowers the yield of 2,2'-azobis(2-methylpropionitrile) as final product. For example, when 2-amino-2-methylpropionitrile containing as impurities some hydrogen cyanide and acetone and 4% by weight of ammonia is reacted with sodium hypochlorite, the yield of oxidative coupling is only 56 mole %.

On the other hand, crude 2-amino-2-methylpropionitrile obtained by the reaction between acetone cyanohydrin and ammonia, or acetone, hydrogen cyanide and ammonia, or acetone and ammonium cyanide, is very unstable particularly in the presence of water. It is therefore difficult to purify crude 2-amino-2-methylpropionitrile in the presence of water produced by reaction so as to satisfy the following conditions: The ammonia content of the purified product be lowered to a sufficient extent; and the decomposition of 2-amino-2-methylpropionitrile be minimized to elevate the yield of the purified product as much as possible.

It may be considered that the difficulty in purifying 2-amino-2-methylpropionitrile can be avoided by limiting the amount of ammonia for the synthesis of aminonitrile to less than the stoichiometric amount based on acetone or hydrogen cyanide, thereby decreasing the ammonia content of the reaction product. Even by this method, however, it is difficult to decrease the ammonia content to a sufficient extent, and besides a decrease in the amount of ammonia naturally leads to undesirable results such as a decrease in the yield of 2-amino-2-methylpropionitrile and an increase in the amount of unreacted acetone or hydrogen cyanide.

In the methods disclosed in J. Am. Chem. Soc. 68, 2628 (1946) and U.S. Pat. No. 2,711,405, purified 2-amino-2-methylpropionitrile is obtained as a high-temperature fraction by distilling the crude reaction product under reduced pressure. By such purification technique, the decomposition of 2-amino-2-methylpropionitrile on distillation is not avoidable, so that the yield of the purified product is naturally lowered. Particularly in the former method, in order to prevent the decomposition of the aminonitrile, a large quantity of potassium hydroxide is added to the crude product, and after the water produced is removed, the crude product is purified by distillation under reduced pressure. Thus, the yield of 2-amino-2-methylpropionitrile is increased but it is only 77 mole %. Further, using a large quantity of potassium hydroxide for the removal of water is disadvantageous economically, so that this method may not be said to be suitable as a commercial process.

The inventors extensively studied to overcome these difficulties, and as a result the following were found: 2-amino-2-methylpropionitrile having an ammonia content of not more than 1.5% by weight can be obtained in a high yield by subjecting crude 2-amino-2-methylpropionitrile (which is obtained by the reaction between acetone cyanohydrin and ammonia, or acetone, hydrogen cyanide and ammonia, or acetone and ammonium cyanide, and contains impurities such as unreacted acetone, hydrogen cyanide and ammonia; water formed by the reaction; and other by-products) to distillation under reduced pressure under conditions such that the temperature of the heat transfer medium be 0° to 50° C. and the pressure be 400 mmHg or less, thereby distilling out a low-boiling fraction comprising ammonia; and 2,2'-azobis(2-methylpropionitrile) is obtained in a high yield by contacting the purified 2-amino-2-methylpropionitrile with an aqueous metal hypochlorite solution which is controlled to a pH of about 10 to 13.5, in an aqueous medium at a temperature of not more than about 30° C., the concentration of the hypochlorite being 5% by weight or less, based on the weight of the reaction mixture, thereby minimizing the decomposition of 2-amino-2-methylpropionitrile.

By this method, the 2,2'-azobis(2-methylpropionitrile) product, which is usable for most usages, can be obtained in a high yield using no expensive hydrazine under mild reaction conditions. However, even such 2,2'-azobis(2-methylpropionitrile) product sometimes has some offensive odor and is not always sufficient in purity to be usable for the polymerization of methyl methacrylate. Of course, its purity can be increased to a sufficient level to be suitable for all usages by recrystallization or washing with a large quantity of water. However, the recrystallization increases the manufacturing cost and leads to a fair loss in the amount, while the washing with water causes waste water problem. Consequently, neither of them is advantageous industrially.

The inventors further studied to solve this problem, and as a result, it was found that 2,2'-azobis(2-methylpropionitrile) of very high purity can be obtained in a high yield by treating the aqueous suspension of 2,2'-azobis(2-methylpropionitrile), which is obtained from the purified 2-amino-2-methylpropionitrile having an ammonia content of not more than 1.5% by weight according to the foregoing inventors' method, with a particular reducing agent.

The present invention provides a process for producing 2,2'-azobis(2-methylpropionitrile) by subjecting 2-amino-2-methylpropionitrile obtained by the reaction between acetone cyanohydrin and ammonia, or acetone, hydrogen cyanide and ammonia, or acetone and ammonium cyanide to oxidative coupling using a metal hypochlorite, which comprises (1) subjecting the crude 2-amino-2-methylpropionitrile obtained by said reaction to distillation under reduced pressure while maintaining the temperature of the heat transfer medium at 0° to 50° C. and the pressure at 400 mmHg or less, whereby a low-boiling fraction comprising ammonia is removed, to obtain a purified 2-amino-2-methylpropionitrile product having an ammonia content of not more than 1.5% by weight, (2) contacting the purified product with an aqueous metal hypochlorite solution at a temperature of not more than about 30° C., the pH of the hypochlorite solution being about 10 to 13.5, and the concentration of the hypochlorite being 5% by weight or less based on the weight of the reaction mixture, and then (3) treating the resulting aqueous suspension of 2,2'-azobis(2-methylpropionitrile) with at least one reducing agent selected from the group consisting of nitrites, sulfites, bisulfites, pyrosulfites, thiosulfates, sulfur dioxide, nitrogen oxide, oxalic acid, formaldehyde, hydrazine, hydrogen peroxide and hydroxylamine.

2-Amino-2-methylpropionitrile used in the present invention is produced by the well-known methods, for example, by the reaction between acetone cyanohydrin (produced by the reaction between acetone and hydrogen cyanide) and ammonia, or acetone, hydrogen cyanide and ammonia, or acetone and ammonium cyanide. When the resulting crude 2-amino-2-methylpropionitrile containing unreacted materials and other impurities is purified according to the process of the present invention, the removal of a low-boiling fraction comprising ammonia by distillation is carried out while maintaining the temperature of the heat transfer medium at 0° to 50° C. When the temperature is higher than 50° C., the decomposition of 2-amino-2-methylpropionitrile or impurities such as hydrogen cyanide is so violent that the yield of 2-amino-2-methylpropionitrile is lowered and besides the reaction solution is coloured markedly. Removing the low-boiling fraction at less than 0° C. is of course possible but no advantages are obtained. The optimum temperature depends upon the pressure, but generally, it is 40° to 50° C. at 200 to 400 mmHg, and 0° to 40° C. at less than 200 mmHg. In order to minimize the decomposition of 2-amino-2-methylpropionitrile and to remove the low-boiling impurities efficiently, it is particularly preferred to carry out the distillation while maintaining the temperature of the heat transfer medium at 10° to 35° C. and the pressure at 150 mmHg or less.

In the purification of crude 2-amino-2-methylpropionitrile according to the process of the present invention, the pressure is maintained at 400 mmHg or less. For distilling out the low-boiling impurities at more than 400 mmHg, the temperature of the heat transfer medium should be raised, which leads to the decomposition of 2-amino-2-methylpropionitrile and to a reduction in its yield. The lower limit of the pressure is not particularly limited, but high vacuum such as less than 5 mmHg has no particular advantages. Industrially, a pressure higher than 5 mmHg is preferred.

The allowable residence time of 2-amino-2-methylpropionitrile in the heating zone is not particularly limited although it depends somewhat upon the temperature of the heat transfer medium. It is, however, preferred to limit the residence time to less than 1 hour in order to keep the decomposition of 2-amino-2-methylpropionitrile at less than 3%. Particularly preferably, the residence time in the heating zone is less than 10 minutes when the temperature of the heat transfer medium ranges from 40° to 50° C.

In the foregoing purification of 2-amino-2-methylpropionitrile, the ammonia content of the purified product is controlled to be at most 1.5% by weight. Ammonia contents of more than 1.5% by weight are not desirable because the yield of the subsequent oxidative coupling becomes poor. Particularly preferably, the ammonia content of purified 2-amino-2-methylpropionitrile is less than 1.0% by weight.

In carrying out the oxidative coupling in which the purified 2-amino-2-methylpropionitrile produced above is contacted with an aqueous metal hypochlorite solution, the pH of the hypochlorite solution is controlled to about 10 to 13.5. The reaction proceeds also when the pH is outside this range, but the yield tends to be lowered.

Further, the concentration of the metal hypochlorite in the reaction system is controlled to be 5% by weight or less. When the concentration is more than 5% by weight, oily substances considered as an intermediate are liberated from the aqueous system, slowing down the rate of reaction extremely and lowering the yield markedly. When the concentration is 5% by weight or less, the liberation of the oily substances is no longer observed and the reaction proceeds smoothly to produce 2,2'-azobis(2-methylpropionitrile) in a high yield.

In the above oxidative coupling, the equivalent ratio of the metal hypochlorite to 2-amino-2-methylpropionitrile is preferably 1.0 to 2.0. The reaction proceeds also at an equivalent ratio of less than 1.0, but it is not desirable in terms of yield. Also, the ratios of more than 2.0 have no advantages. Generally, the equivalent ratios within a range of 1.2 to 1.8 provide a particularly preferred result.

The oxidative coupling is preferably carried out at about $-5°$ to about $30°$ C. The reaction can be carried out at a temperature of less than $-5°$ C., but there occurs the danger of the aqueous phase being frozen. When the temperature is higher than $30°$ C., the yield becomes poor owing to side reactions and decomposition of 2,2'-azobis(2-methylpropionitrile). Particularly preferably, the reaction temperature is $0°$ to $20°$ C.

The metal hypochlorite used in the oxidative coupling includes, for example, sodium hypochlorite, potassium hypochlorite and calcium hypochlorite. Of these hypochlorites, sodium hypochlorite is desirable for economical reasons.

As equipment used for the purification of crude 2-amino-2-methylpropionitrile according to the process of the present invention, conventional types such as wetted wall towers (thin-film evaporation type), packing towers, tray towers and flash towers may be usable, but the purification of the present invention is not limited by the equipment used therefor.

Further, the purification of 2-amino-2-methylpropionitrile may be carried out either continuously or batchwise. Ammonia, hydrogen cyanide, acetone and a part of 2-amino-2-methylpropionitrile, which are distilled out as a low-boiling fraction or purification, may be recovered and re-used. The methods for recovering and recycling the components in the low-boiling fraction are well-known in the art and not particularly limited.

As the reducing agent used in the reduction treatment of the present invention, there may be exemplified sulfur dioxide, nitrogen oxide, salts capable of dissociating in an aqueous system to produce anionic ions such as nitrite, sulfite, bisulfite, pyrosulfite and thiosulfate ions (e.g. alkali metal salts, alkaline earth metal salts or ammonium salts of the foregoing anionic ions) and the like. Further, oxalic acid, formaldehyde, hydrazine, hydrogen peroxide and hydroxylamine may be used as the reducing agent. Of these compounds, sodium sulfite, sodium bisulfite and sulfur dioxide are particularly preferred. These reducing agents may be used alone or in combination.

The amount of the reducing agent used is determined as follows: After the oxidative coupling is finished, a part of the resulting reaction mixture sampled is added to a acidified potassium iodide solution, followed by titration, preferably, with 0.1 N aqueous sodium thiosulfate solution. By this operation, the iodide is converted to free iodine by the action of oxidative components in the reaction mixture, and the free iodine is again reduced to an iodide by the action of thiosulfate. The amount of the reducing agent is about 1.0 to about 3.0 equivalents or more per equivalent of the oxidative components. Particularly preferably, the amount is 1.3 to 3.0 equivalents per equivalent of the oxidative components.

The optimum pH at which the reduction treatment is carried out is not particularly limited, although it depends somewhat upon the kinds of reducing agent. Generally, however, acidic conditions are preferred. Particularly, when inorganic reducing agents are used, acidic conditions below a pH of 6.5 provide a more desirable results in a short time. The pH of the reaction mixture to be reduced may be adjusted, if necessary, for example, with a conventional acid such as sulfuric acid or hydrochloric acid. When reducing agents such as sulfur dioxide and sodium bisulfite are used, the agents themselves act as an acidifying agent.

The temperature of the reduction treatment is not particularly limited, though generally, temperatures between $0°$ C. and $30°$ C. are preferred. The time required for the reduction treatment is not particularly limited, although it depends somewhat upon the kind of reducing agents and treating method. Generally, however, the treatment comes to an end within 2 hours. The treatment sometimes comes to an end within only a few minutes under desirable conditions.

After the reduction treatment, precipitated 2,2'-azobis(2-methylpropionitrile) crystals are filtered and washed with some water. A product of very high purity can thus be obtained by a simple operation.

By the reduction treatment of the present invention, oxidative impurities mainly produced during the oxidative coupling of 2-amino-2-methylpropionitrile are decomposed, and consequently, 2,2'-azobis(2-methylpropionitrile) is produced in such a high purity that special purification such as recrystallization can be omitted. Further surprisingly, some oily impurities considered as intermediates, by-products or mixture thereof are also decomposed by the reduction treatment, so that 2,2'-azobis(2-methylpropionitrile) becomes easy to crystallize. Thus, 2,2'-azobis(2-methylpropionitrile) can be obtained in a high yield in the form of crystals having a free-flowing property. Further unexpectedly, the foregoing reducing agents act also as a deodorizing and decolouring agent, so that 2,2'-azobis(2-methylpropionitrile) can be obtained as pure-white, almost odorless crystals by the reduction treatment of the present invention.

2,2'-Azobis(2-methylpropionitrile) synthesized and reduction-treated according to the present invention, has a purity high enough to be usable for almost all usages.

The present invention will be illustrated in more detail with reference to the following Examples, which are not, however, to be interpreted as limiting the invention thereto. In the Examples, all percentages are by weight unless otherwise specified.

EXAMPLE 1

Liquid ammonia (121 g) was placed in a 1-liter autoclave, and acetone cyanohydrin (434 g) having a purity of 92% was charged thereinto under pressure. Reaction was carried out at 25° C. for 10 hours with stirring at a rate of 300 rpm to produce 2-amino-2-methylpropionitrile. The reaction mixture was withdrawn from the autoclave and distilled at 35° C. (the temperature of the heat transfer medium) and at 60 mmHg in a wetted wall tower, whereby a low-boiling fraction was distilled out to obtain purified 2-amino-2-methylpropionitrile. The residence time of the reaction mixture in the heating zone was less than 1 minute. The resulting purified product had an ammonia content of 0.4%, a hydrogen cyanide content of 0.5% and an acetone content of 0.7%. The purity of the purified product was 79% by weight, and a main impurity in the product was water. The yield of 2-amino-2-methylpropionitrile was 92.0 mole % based on acetone cyanohydrin.

An aqueous solution (1330 g) containing 3% of sodium hypochlorite was adjusted to a pH of 11.5 and cooled to 5° C. Thereafter, the purified 2-amino-2-methylpropionitrile (38 g) having a purity of 79% was added thereto over 30 minutes with stirring. The equivalent ratio of sodium hypochlorite to 2-amino-2-methylpropionitrile was 1.5. The reaction mixture was stirred at 5° to 10° C. for 20 minutes.

The slurry-like reaction mixture containing precipitated 2,2'-azobis(2-methylpropionitrile) was sampled and subjected to iodometry, and it was found that the total amount of oxidative substances was 0.07 equivalent. The reaction mixture was then adjusted to a pH of 6 with a dilute sulfuric acid, and 20% aqueous sodium bisulfite solution (50 g, 0.19 equivalent) was added thereto, followed by stirring at 15° C. for 30 minutes.

Thereafter, the resulting white crystals were filtered, washed with a small amount of water and dried to obtain 28 g of 2,2'-azobis(2-methylpropionitrile). The yield was 95.6 mole % based on 2-amino-2-methylpropionitrile and 88 mole % based on acetone cyanohydrin. The product was analyzed by iodometry, and it was found that the amount of oxidative impurities was less than 100 ppm. The purity of the product was more than 99.5% by the nitrogen gas measuring method. The crystal was completely pure-white and almost odorless. Melting point, 105°–106° C.

EXAMPLE 2

Purified 2-amino-2-methylpropionitrile was produced in the same manner as in Example 1, except that the purification was carried out in a different way. By operating a flash tower at 43° C. and at 320 mmHg, a low-boiling fraction comprising ammonia was removed at the top of the tower and purified 2-amino-2-methylpropionitrile was obtained at the bottom. The purified product was a yellowish brown liquid and its composition was as follows: 2-Amino-2-methylpropionitrile, 81%; ammonia, 0.3%; hydrogen cyanide, 0.4%; acetone, 0.8%; and the rest, impurities comprising water. The yield ws 93 mole % based on acetone cyanohydrin.

2,2'-Azobis(2-methylpropionitrile) was produced by the same oxidative coupling as in Example 1, except that the above purified 2-amino-2-methylpropionitrile (37 g) having a purity of 81% was used. After the reaction was finished, the reaction mixture was sampled and measured for oxidative substances by iodometry, and it was found that the amount of the substances was 0.09 equivalent.

The reaction mixture was adjusted to a pH of 7 with a dilute sulfuric acid and reduction-treated by bubbling 0.27 equivalent of sulfur dioxide gas into the mixture, followed by stirring at 10° C. for 20 minutes. Thereafter, the white crystals were filtered, washed with water and dried to obtain 28.2 g of 2,2'-azobis(2-methylpropionitrile). The yield was 96.4% based on 2-amino-2-methylpropionitrile, and the overall yield was 89.7% based on acetone cyanohydrin. The 2,2'-azobis(2-methylpropionitrile) obtained was an almost odorless, very free-flowing, white crystal and had a purity of 99.7%. The content of oxidative impurities was less than 100 ppm.

COMPARATIVE EXAMPLE 1

In the same manner as in Example 1, 2-amino-2-methylpropionitrile was synthesized by reacting liquid ammonia (121 g) with 92%-purity acetone cyanohydrin (434 g) in an autoclave. The reaction mixture contained 72% of 2-amino-2-methylpropionitrile and 4% of ammonia.

2,2'-Azobis(2-methylpropionitrile) was produced in the same manner as in Example 1, except that the unpurified reaction mixture (40 g) of 2-amino-2-methylpropionitrile obtained above was used. Thus, 15.7 g of 2,2'-azobis(2-methylpropionitrile) was obtained. The yield was 56 mole % based on 2-amino-2-methylpropionitrile.

COMPARATIVE EXAMPLE 2

The synthesis, purification and oxidative coupling of 2-amino-2-methylpropionitrile were carried out in the same manner as in Example 1. After the oxidative coupling was finished, the precipitated crystals in the reaction mixture were filtered without applying the reduction treatment to the mixture. The crystals were then washed with water and dried to obtain 2,2'-azobis(2-methylpropionitrile). The yield was 94 mole % based on 2-amino-2-methylpropionitrile, and the purity was 98.5%. The content of oxidative impurities in the product was as much as 3200 ppm as measured by iodometry. This crystal had a fairly offensive odor and was coloured pale yellow and poor in a free-flowing property, so that recrystallization from methanol was required to give it a commercial value.

EXAMPLE 3

Liquid ammonia (130 g) and 95%-purity acetone cyanohydrin (430 g) were placed in an autoclave, and reaction was carried out at 25° C. for 9 hours with stirring to produce 2-amino-2-methylpropionitrile. The reaction mixture was transferred to a rotary evaporator, and a low-boiling fraction containing ammonia, hydrogen cyanide and acetone was distilled away from the mixture over 30 minutes while operating the evaporator at 25° C. (the temperature of the heat transfer medium) and at 30 mmHg. Purified 2-amino-2-methylpropionitrile was obtained as a high-boiling residue, and it had the following composition: 2-Amino-2-methylpropionitrile, 86%; ammonia, 0.3%; hydrogen cyanide, 0.3%; and the rest, impurities comprising water. The yield was 93 mole % based on acetone cyanohydrin.

The purified 2-amino-2-methylpropionitrile thus obtained (95 g, 0.97 mole) and 4% aqueous sodium hypochlorite solution (2350 g, 1.26 mole), which was previously adjusted to a pH of 12.0 and cooled to 5° C., were added separately to a reactor over 1 hour so that the addition of the two was finished at the same time. During that time, the reaction temperature was kept at 5° to 10° C. by cooling the outside of the reactor. After the addition, the reaction mixture was stirred for a further 15 minutes. The resulting aqueous suspension of 2,2′-azobis(2-methylpropionitrile) crystals was sampled and measured for the content of oxidative substances by iodometry. As a result, the content was 0.15 equivalent.

The aqueous suspension was adjusted to a pH of 5 with a dilute hydrochloric acid and reduction-treated at 10° C. for 1 hour with stirring with addition of a 20% aqueous sodium nitrite solution (65g, 0.38 equivalent). Thereafter, the white crystals were filtered, washed with water and dried to obtain 75.5 g of 2,2′-azobis(2-methylpropionitrile). The yield was 94.7 mole % based on 2-amino-2-methylpropionitrile, and the overall yield was 88 mole % based on acetone cyanohydrin. The 2,2′-azobis(2-methylpropionitrile) obtained was a white, almost odorless and very free-flowing powder. The content of oxidative impurities was less than 100 ppm. The purity was 99.8% as measured by the nitrogen gas measuring method.

What is claimed is:

1. A process for producing 2,2′-azobis(2-methylpropionitrile) by subjecting 2-amino-2-methylpropionitrile obtained by the reaction between acetone cyanohydrin and ammonia, or acetone, hydrogen cyanide and ammonia, or acetone and ammonium cyanide to oxidative coupling using a metal hypochlorite, which comprises (1) subjecting the crude 2-amino-2-methylpropionitrile obtained by said reaction to distillation at a temperature of the heat transfer medium of 0° to 50° C. and a pressure of 400 mmHg or less to obtain a purified 2-amino-2-methylpropionitrile product having an ammonia content of 1.5% by weight or less, (2) contacting the purified product with an aqueous metal hypochlorite solution at a temperature of not more than about 30° C., the pH of the hypochlorite solution being about 10 to 13.5 and the concentration of the metal hypochlorite being 5% by weight or less based on the weight of the reaction mixture, and then (3) treating the resulting aqueous suspension of 2,2′-azobis(2-methylpropionitrile) with at least one reducing agent selected from the group consisting of nitrites, sulfites, bisulfites, pyrosulfites, thiosulfates, sulfur dioxide, nitrogen oxide, oxalic acid, formaldehyde, hydrazine, hydrogen peroxide and hydroxylamine.

2. A process according to claim 1, wherein said distillation is carried out at a temperature of the heat transfer medium of 10° to 35° C. and a pressure of 150 mmHg or less to obtain a purified 2-amino-2-methylpropionitrile product having an ammonia content of 1.0% by weight or less.

3. A process according to claim 1, wherein said reducing agent used in the step (3) is sodium sulfite, sodium bisulfite or sulfur dioxide.

4. A process according to claim 1, wherein the treatment with a reducing agent in the step (3) is carried out at a pH of 6.5 or less.

* * * * *